(12) United States Patent
Visurraga, Jr.

(10) Patent No.: US 11,832,800 B2
(45) Date of Patent: Dec. 5, 2023

(54) MEDICAL VISUALIZATION AND INTUBATION SYSTEMS

(71) Applicant: Visurraga Enterprises, LLC, Hyattsville, MD (US)

(72) Inventor: Cesar Jesus Steven Visurraga, Jr., Hyattsville, MD (US)

(73) Assignee: Visurraga Enterprises LLC, Hyattsville, MD (US)

( * ) Notice: Subject to any disclaimer, the term of this patent is extended or adjusted under 35 U.S.C. 154(b) by 0 days.

(21) Appl. No.: 17/899,789

(22) Filed: Aug. 31, 2022

(65) Prior Publication Data

US 2023/0248232 A1 Aug. 10, 2023

Related U.S. Application Data

(60) Provisional application No. 63/336,069, filed on Apr. 28, 2022, provisional application No. 63/267,779, filed on Feb. 9, 2022.

(51) Int. Cl.
*A61B 1/267* (2006.01)
*A61B 1/04* (2006.01)
*A61B 1/05* (2006.01)
*A61B 1/06* (2006.01)
*A61B 1/00* (2006.01)

(52) U.S. Cl.
CPC .............. *A61B 1/05* (2013.01); *A61B 1/0008* (2013.01); *A61B 1/00052* (2013.01); *A61B 1/00114* (2013.01); *A61B 1/00124* (2013.01); *A61B 1/0655* (2022.02); *A61B 1/0684* (2013.01); *A61B 1/267* (2013.01)

(58) Field of Classification Search
CPC ......... A61B 1/267; A61B 1/05; A61B 1/0655; A61B 1/00052; A61B 1/0008; A61B 1/00114; A61B 1/00124; A61B 1/0684
USPC .................... 600/184–185, 188, 194, 199
See application file for complete search history.

(56) References Cited

U.S. PATENT DOCUMENTS

| | | | |
|---|---|---|---|
| 6,115,523 | A | 9/2000 | Choi et al. |
| 6,319,195 | B1 | 11/2001 | Nakaichi et al. |
| 7,946,981 | B1 | 5/2011 | Cubb |
| 8,479,739 | B2 | 7/2013 | Hirsh |

(Continued)

FOREIGN PATENT DOCUMENTS

| | | |
|---|---|---|
| WO | 2020210327 A1 | 10/2020 |
| WO | 2021170626 A1 | 9/2021 |

OTHER PUBLICATIONS

United States Patent and Trademark Office, PCT/US2023/012278, PCT International Search Report and Written Opinion, dated Feb. 3, 2023.

(Continued)

*Primary Examiner* — Jessica Weiss
(74) *Attorney, Agent, or Firm* — Leveque IP Law, P.C.

(57) ABSTRACT

A laryngoscope enhancement system (LES) and an intubation system including an LES are provided. The LES includes a holder and a video stylet. The holder includes an adjustable mount to releasably secure an electronic device with a display, and an end cap configured to removably attach the holder to an upper end of a laryngoscope handle. The video stylet includes a connecter removably attachable to the electronic device, a flexible segment, a malleable segment and a video camera.

20 Claims, 11 Drawing Sheets

(56) References Cited

U.S. PATENT DOCUMENTS

| | | | |
|---|---|---|---|
| 8,652,033 B2* | 2/2014 | Berci | A61B 1/0005 |
| | | | 600/199 |
| D724,725 S | 3/2015 | Chang | |
| 8,972,714 B2 | 3/2015 | Talbert et al. | |
| 9,179,831 B2 | 11/2015 | McGrail et al. | |
| 9,199,051 B2 | 12/2015 | Booth | |
| 9,295,378 B2 | 3/2016 | Nearman et al. | |
| 9,427,543 B2 | 8/2016 | Wei et al. | |
| 9,579,476 B2 | 2/2017 | Stocking et al. | |
| 9,662,466 B2 | 5/2017 | Gunday et al. | |
| 9,681,797 B2 | 6/2017 | Scherr et al. | |
| 10,182,712 B2 | 1/2019 | Matthes | |
| 10,285,580 B2 | 5/2019 | Brambrink et al. | |
| 10,368,732 B2 | 8/2019 | Law et al. | |
| 10,588,498 B2 | 3/2020 | Dan et al. | |
| 10,729,317 B2 | 8/2020 | Eggli et al. | |
| 10,744,288 B2 | 8/2020 | Runnels | |
| 11,064,877 B2 | 7/2021 | Galloway et al. | |
| 2002/0022769 A1* | 2/2002 | Smith | A61B 1/015 |
| | | | 600/188 |
| 2003/0195390 A1 | 10/2003 | Graumann | |
| 2005/0182297 A1 | 8/2005 | Gravenstein et al. | |
| 2010/0261967 A1* | 10/2010 | Pacey | A61B 1/00142 |
| | | | 600/188 |
| 2011/0028790 A1* | 2/2011 | Farr | A61B 1/0676 |
| | | | 600/187 |
| 2011/0137127 A1* | 6/2011 | Schwartz | A61B 1/05 |
| | | | 600/188 |
| 2011/0178372 A1* | 7/2011 | Pacey | A61B 1/00142 |
| | | | 600/188 |
| 2012/0078055 A1* | 3/2012 | Berci | A61B 1/267 |
| | | | 600/188 |
| 2012/0162401 A1 | 6/2012 | Melder et al. | |
| 2015/0190044 A1* | 7/2015 | Livnat | A61B 1/267 |
| | | | 600/188 |
| 2016/0051781 A1* | 2/2016 | Isaacs | A61B 1/00066 |
| | | | 600/188 |
| 2020/0178786 A1 | 6/2020 | Sabetrasekh et al. | |
| 2020/0359883 A1 | 11/2020 | Livnat | |
| 2021/0219834 A1* | 7/2021 | Velez Rivera | A61B 1/05 |
| 2023/0137933 A1* | 5/2023 | Gros | A61B 1/00052 |
| | | | 600/188 |

OTHER PUBLICATIONS https://cults3d.com/en/3d-model/tool/video-laringoscope, downloaded from internet Mar. 9, 2023.

https://smartblade.co.za/, downloaded from the internet on Mar. 9, 2023.

https://www.aummedtech.com/video-laryngoscopes-covid-warriors/, downloaded from the internet on Mar. 9, 2023.

https://www.hullanesthesia.com/p/1031/ainca-video-stylet-with-monitor-and-charger, Downloaded from the internet on Mar. 9, 2023.

https://www.imedicalapps.com/2016/04/iphone-intubation-video-laryngoscopy-vlstreaming-adaptor/, downloaded from the internet on Mar. 9, 2023.

Matek J, Kolek F, Klementova O, Michalek P, Vymazal T. Optical Devices in Tracheal Intubation-State of the Art in 2020. Diagnostics (Basel). Mar. 22, 2021;11(3):575. doi: 10.3390/diagnostics11030575. PMID: 33810158; PMCID: PMC8004982.

* cited by examiner

MEDICAL VISUALIZATION AND INTUBATION SYSTEMS

CROSS-REFERENCE TO RELATED APPLICATIONS

This application claims the benefit of U.S. Provisional Patent Application Nos. 63/267,779 (filed on Feb. 9, 2022) and 63/336,069 (filed on Apr. 28, 2022), the contents of which are incorporated herein by reference in their entireties.

BACKGROUND

The present disclosure relates to medical devices. More particularly, the present disclosure relates to a medical visualization and intubation systems.

Laryngoscopy may be performed for many reasons, such as, for example, to view the interior structure of the throat such as the larynx, to facilitate endotracheal intubation using an endotracheal tube (ETT), to perform a biopsy procedure, etc. Generally, direct laryngoscopy refers to the use of a handheld laryngoscope to view the interior structure of the throat along a direct line-of-sight, while indirect laryngoscopy refers to the use of a laryngoscope in combination with an optical device to visualize the larynx or trachea along an indirect line-of-sight, such as, for example, a mirror or prism, a fiberoptic stylet, a video laryngoscope, etc.

However, for certain medical procedures, direct laryngoscopy often presents challenges that make a direct line-of-sight view difficult due to planned or unplanned scenarios such as anterior vocal cords, obesity, large tongue, or other irregular airway anatomical features.

DETAILED DESCRIPTION

Figure 1:
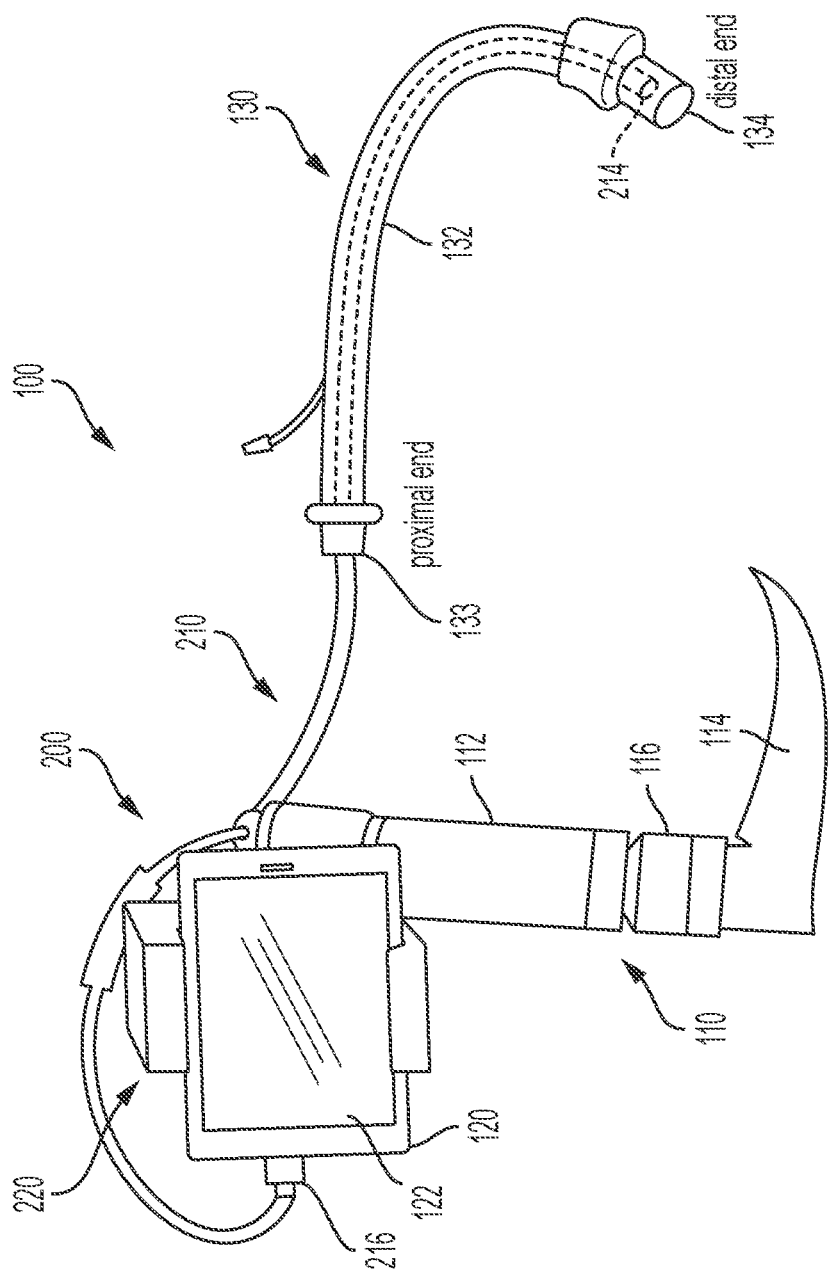
FIG. 1 depicts an intubation system (IS), in accordance with an embodiment of the present disclosure.

Embodiments of the present disclosure will now be described with reference to the drawing figures, in which like reference numerals refer to like parts throughout.

Embodiments of the present disclosure advantageously provide a system that broadens the use of a standard laryngoscope beyond direct laryngoscopy to video-based, indirect laryngoscopy for various medical procedures, such as, for example, intubation, visualization, etc.

In one embodiment, a laryngoscope enhancement system includes a holder and a video stylet. The holder includes an adjustable mount and an end cap. The adjustable mount is configured to releasably secure an electronic device with a display. The end cap is fixedly connected to the adjustable mount, and defines a central cavity with a lower opening. The end cap is configured to removably attach the holder to an upper end of a laryngoscope handle, and the lower opening has a diameter conforming to a diameter of the upper end of the laryngoscope handle. The video stylet includes a number of wires, a connecter coupled to the wires, a flexible segment, a malleable segment and a video camera coupled to one or more of the wires. The connector is removably attachable to an electronic device. The flexible segment includes a flexible sheath enclosing the wires. The malleable segment includes a malleable sheath enclosing a malleable wire and the wires. The malleable sheath has a smaller diameter than the flexible sheath.

FIG. 1 depicts IS 100, in accordance with an embodiment of the present disclosure.

In many embodiments, IS 100 includes laryngoscope 110, electronic device 120, ETT 130 and LES 200.

Laryngoscope 110 includes handle 112, blade 114 and connector 116 that attaches blade 114 to the lower end of handle 112. Connector 116 may be fixed, or releasable in order to support different sizes and types of blades 114. For example, a portion of connector 116 may be fixed to, or incorporated within, the lower end of handle 112, a mating portion of connector 116 may be fixed to, or incorporated within, the proximal end of blade 114. Blade 114 may be a Macintosh (curved) blade, a Miller (straight) blade, etc., and generally includes a spatula to pass over the lingual surface of the tongue, a flange to displace the tongue, and a tip to lift the epiglottis. Handle 112 is cylindrical in shape with a generally uniform diameter, and has an upper end as well as the lower end.

Electronic device 120 includes display 122 for displaying images from video stylet 210. More particularly, electronic device 120 is a portable, handheld, computer-based electronic device with a touchscreen interface and a data/charging port (e.g., a Lighting port, a USB-C port, etc.), such as, for example, a smartphone (e.g., Apple iPhone, Samsung Galaxy S/A/Z, etc.), a tablet (e.g., Apple iPad mini, Samsung Galaxy Tab, etc.), etc. In some embodiments, electronic device 120 may include a network interface to connect to a cellular network, a WiFi network, etc.

ETT 130 includes, inter alia, tube 132, proximal endcap 133 defining a proximal opening, and beveled distal end 134 defining a distal opening.

LES 200 includes video stylet 210 and holder 220 for electronic device 120. Video stylet 210 includes, inter alia, connector 216 that is removably attachable to the data/charging port of electronic device 120, a flexible segment (depicted in solid line) generally disposed outside tube 132, a malleable segment (depicted in dotted line) generally disposed within tube 132, and video camera 214. The malleable segment of video stylet 210 is deformable into a preferred shape or curvature, and may extend past the proximal end of ETT 130, i.e., outside tube 132. The combination of a flexible segment and a malleable segment in video stylet 210 is advantageously lightweight and maneuvers easily when advancing ETT 130 into the patient's airway with one hand.

Figure 2:
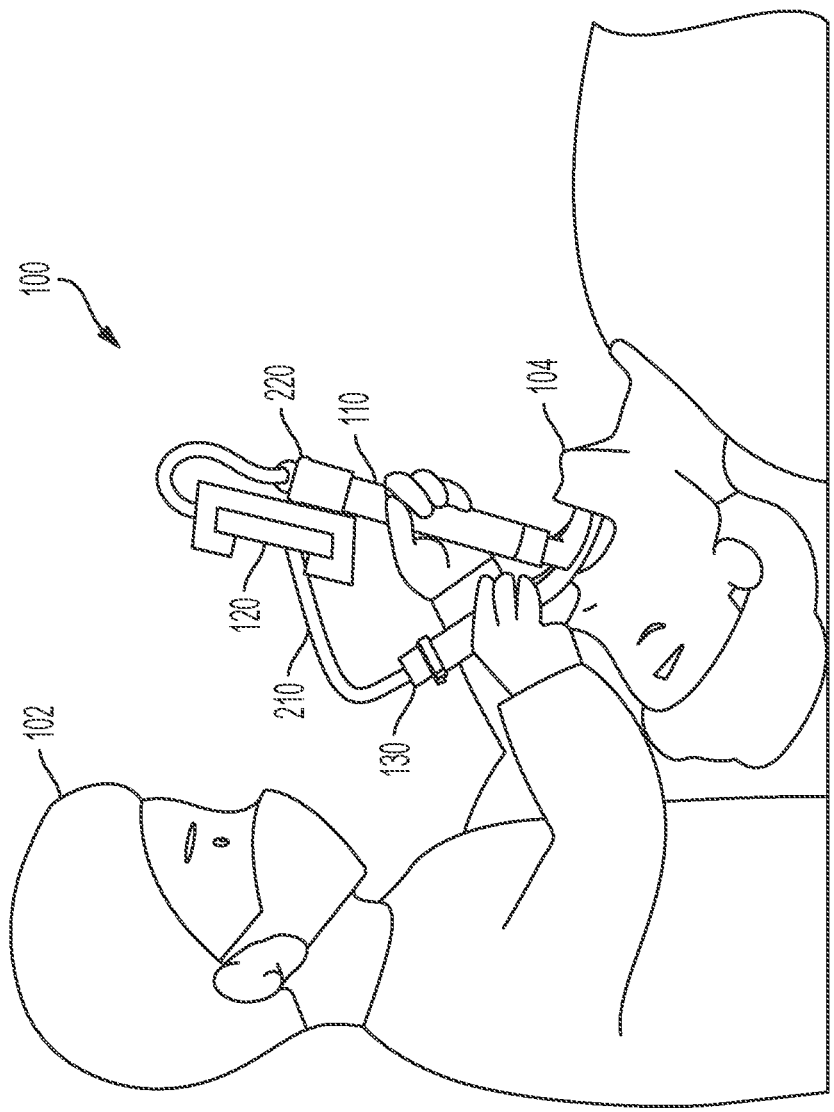
FIG. 2 depicts in-situ operation of an IS, in accordance with an embodiment of the present disclosure.

FIG. 2 depicts in-situ operation of IS 100, in accordance with an embodiment of the present disclosure.

During an intubation procedure for patient 104, healthcare provider 102 holds handle 112 of laryngoscope 110 in one hand and tube 132 of ETT 130 in the other hand. More particularly, healthcare provider 102 first manipulates video stylet 210 into a preferred curvature, and then inserts video stylet 210 into the opening defined by proximal endcap 133 of ETT 130 such that video camera 214 is disposed proximate to the opening defined by beveled distal end 134 of ETT 130. Once inserted, ETT 130 generally conforms to the curvature of the malleable portion of video stylet 210. With the assistance of laryngoscope 110, healthcare provider 102 introduces ETT 130 into the mouth of patient 104. After initially positioning ETT 130, healthcare provider 102 then advances ETT 130 towards the vocal cords of patient 104 using indirect laryngoscopy, during which time images of the upper airway, captured by video camera 214, are presented on display 122 for viewing by healthcare provider 102.

During a visualization procedure for patient 104, ETT 130 is not used and healthcare provider 102 holds handle 112 of laryngoscope 110 in one hand and video stylet 210 in the other hand. More particularly, with the assistance of laryngoscope 110, healthcare provider 102 introduces video stylet 210 into the mouth of patient 104. After initially positioning video stylet 210, healthcare provider 102 then advances video stylet 210 towards the vocal cords of patient 104 using indirect laryngoscopy, during which time images of the upper airway, captured by video camera 214, are presented on display 122 for viewing by healthcare provider 102.

IS 100 advantageously incorporates the same handheld laryngoscope into these procedures, which allows healthcare provider 102 to perform the same physical movements as before while integrating indirect line-of-sight capability.

Figure 3:
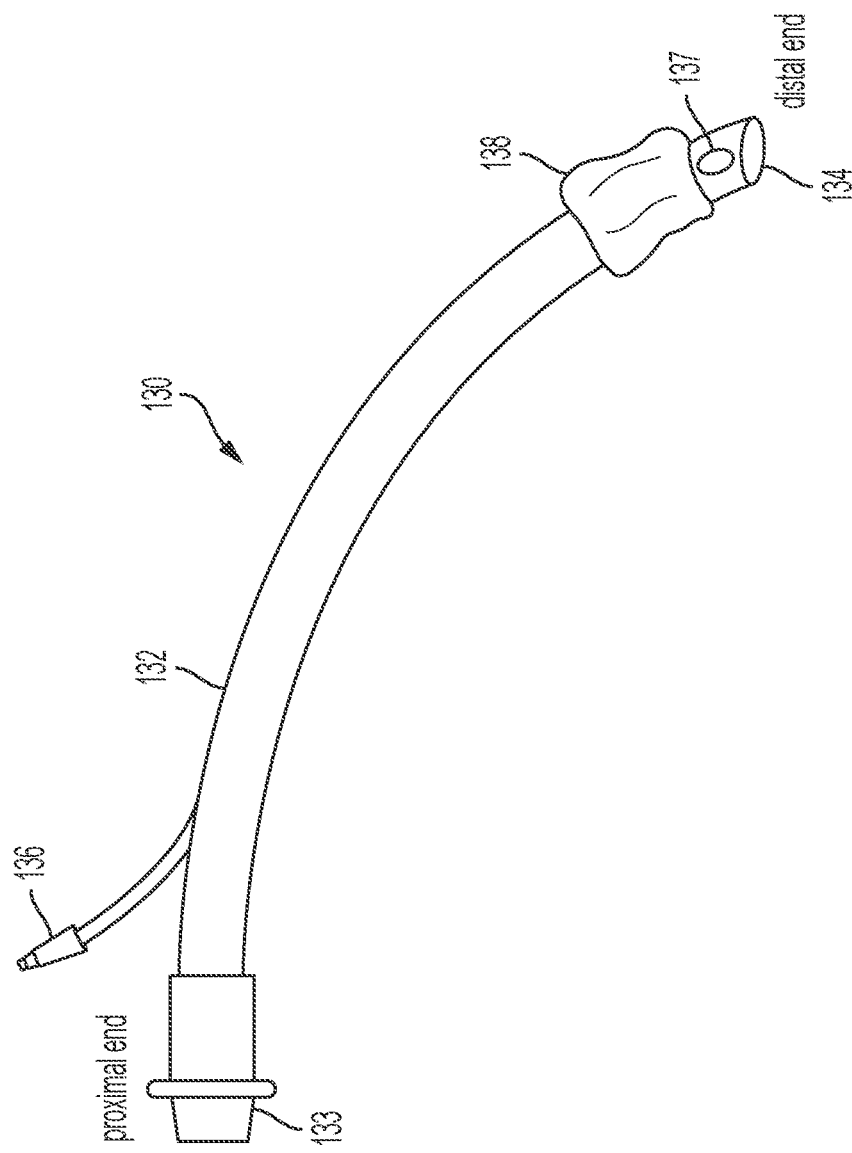
FIG. 3 depicts an ETT, in accordance with an embodiment of the present disclosure.

FIG. 3 depicts ETT 130, in accordance with an embodiment of the present disclosure.

ETT 130 includes tube 132, proximal endcap 133 defining a proximal opening, beveled distal end 134 defining a distal opening, air supply connector 136, and inflatable cuff/balloon 138. Opening 137 (e.g., a "Murphy eye") may also be provided at the distal end of tube 132 to prevent obstruction if the distal opening defined by beveled distal end 134 is blocked by mucus or sealed by contact with the patient's tracheal wall.

The proximal opening accepts video stylet 210 for passage through tube 132, while the distal opening allows video camera 214 to extend past beveled distal end 134 (if desired). Generally, tube 132 has an outer diameter and an inner diameter, and ETT 130 has a size (in millimeters) that is based on the inner diameter of tube 132, generally ranging from 3.5 (i.e., 3.5 mm inner diameter, e.g., for small infants) to 8.5 (i.e., 8.5 mm inner diameter, e.g., for adult males), and larger. The sizes are typically specified in 0.5 mm increments.

Figure 4:
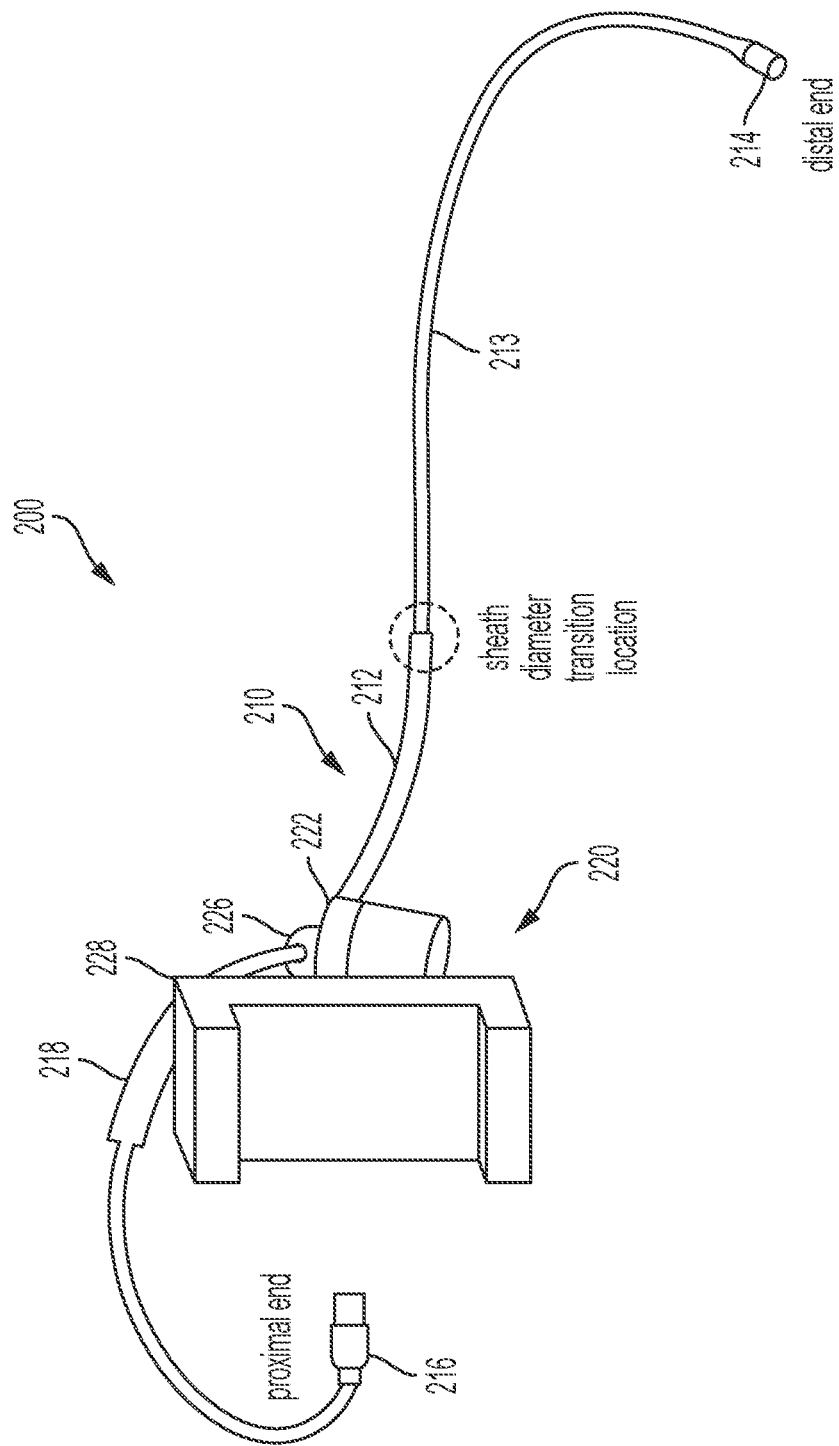
FIG. 4 depicts a laryngoscope enhancement system (LES), in accordance with an embodiment of the present disclosure.

FIG. 4 depicts LES 200, in accordance with an embodiment of the present disclosure.

LES 200 includes video stylet 210 and holder 220 for electronic device 120.

Generally, video stylet 210 includes connector 216 that is removably attachable to the data/charging port of electronic device 120, a flexible portion, i.e., tube or sheath 212, a malleable portion, i.e., tube or or sheath 213, and video camera 214. In many embodiments, a light source (not depicted for clarity) may be co-located with video camera 214. In certain embodiments, light source control unit 218 is coupled to one or more of the wires to control the light source, such as, for example, one or more light-emitting diodes (LEDs), etc. Light source control unit 218 may include a dial, button(s), slider, etc. to control the intensity of the light source.

Holder 220 includes end cap 222 and adjustable mount 228. In many embodiments, holder 220 may also include guide 226 to support a portion of video stylet 210. In the embodiment depicted in FIG. 4, guide 226 is disposed on an upper portion of end cap 222; other locations are also supported.

Figure 5A:
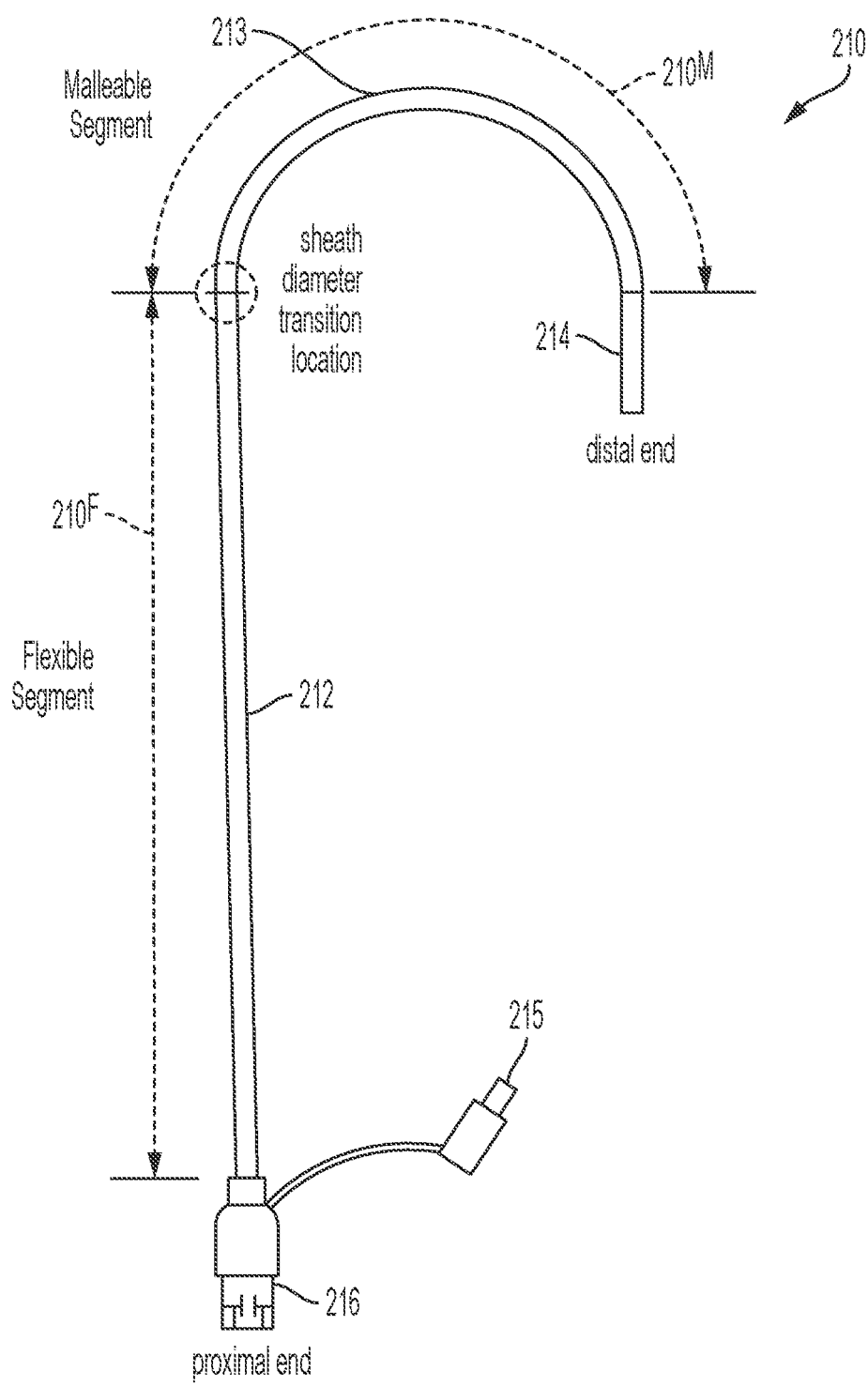
FIGS. 5A, 5B and 5C depict a video stylet of an LES, in accordance with an embodiment of the present disclosure.
Figure 5B:
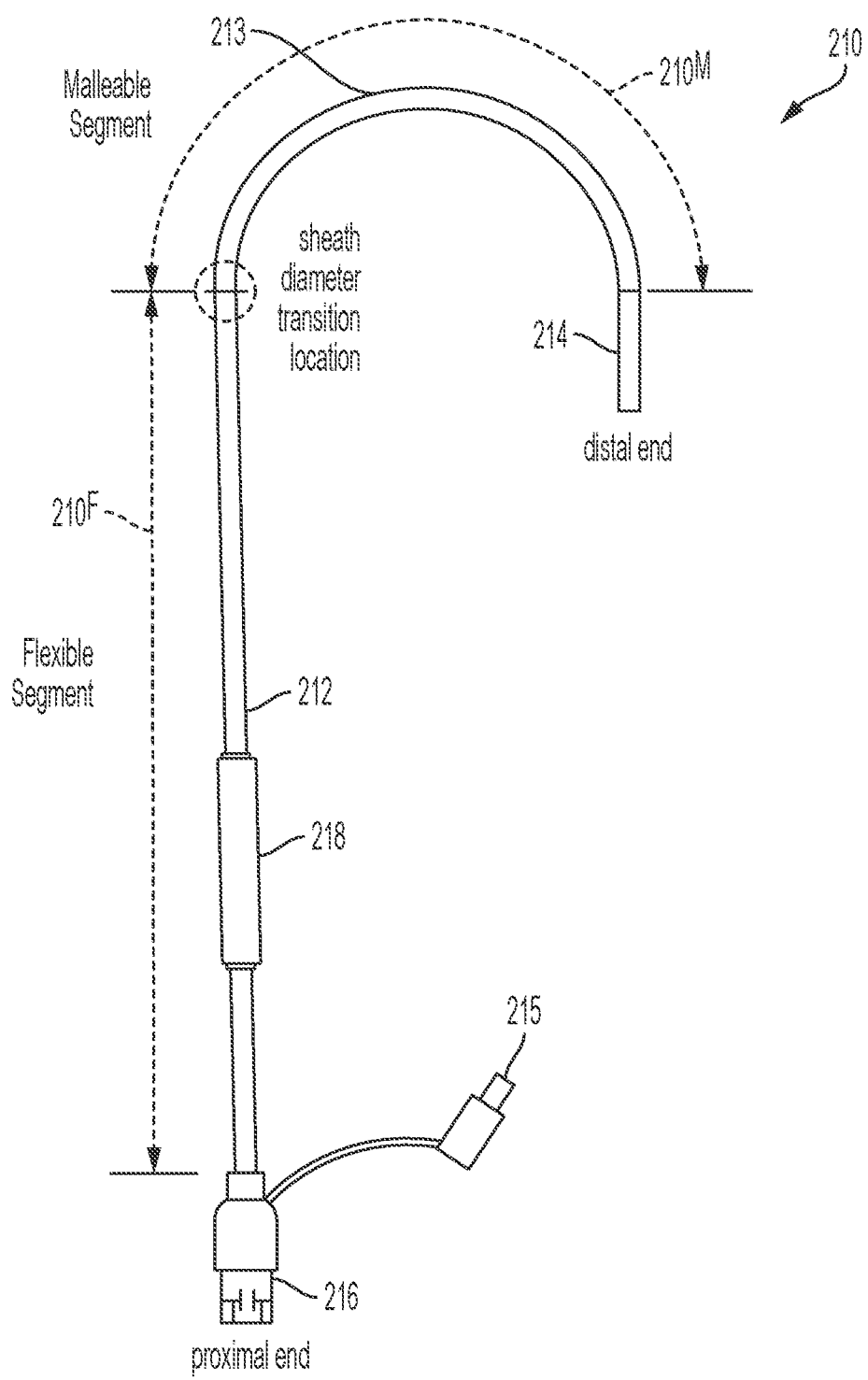
Figure 5C:
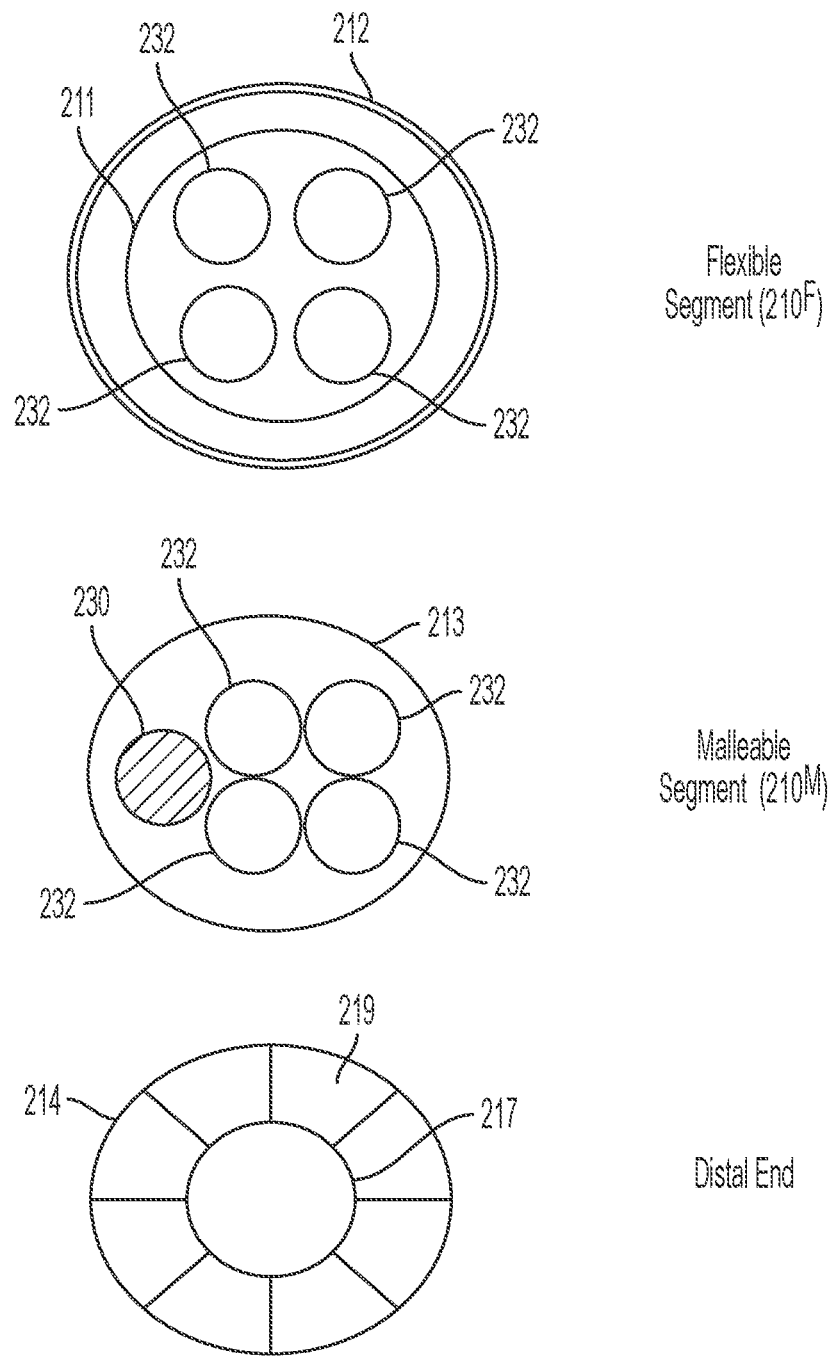

FIGS. 5A, 5B and 5C depict video stylet 210, in accordance with embodiments of the present disclosure.

More particularly, FIGS. 5A and 5B depict plan views of video stylet 210, in accordance with embodiments of the present disclosure, while FIG. 5C depicts a cross-sectional view of the flexible segment of video stylet 210, a cross-sectional view of the malleable segment of video stylet 210, and a view of the distal end of video stylet 210, in accordance with embodiments of the present disclosure.

Video stylet 210 has a proximal end, flexible segment 210F, a sheath diameter transition location, a malleable segment 210*m*, and a distal end. In many embodiments, video stylet has an overall length of about 33 to 42 inches, flexible segment 210F has a diameter of about 7 to 12 mm and a length of about 16 to 20 inches, malleable segment 210*m* has a diameter of about 3 to 6.5 mm and a length of about 16 to 20 inches, and video camera 214 has a diameter of about 3 to 5.5 mm and a length of about 1 to 2 inches.

A number of wires 232 couple connector 216 to video camera 214, and extend through flexible segment 210F and malleable segment 210*m*. Generally, the number of wires 232 are determined by a particular electrical communication specification, such as, for example, Universal Serial Bus (USB), etc. Connector 216 is coupled to the wires at the proximal end of video stylet 210. Sheath 212 encloses the wires, and extends along the length of flexible segment 210F, i.e., from connector 216 to the sheath diameter transition location. Sheath 213 encloses a malleable wire and the wires, and extends along the length of malleable segment 210*m*, i.e., from the sheath diameter transition location to the video camera 214. Advantageously, sheath 213 has a smaller diameter than sheath 212 to accommodate small diameter ETTs 130.

In certain embodiments, an additional connector 215 may be coupled the wires at the proximal end of video stylet 210. Additional connector 215 may have a different electrical interface than connector 216, and may be coupled to an additional electronic device, such as, for example, a smartphone, tablet, large screen monitor, etc. In other embodiments, the electrical interfaces may be the same for connectors 215 and 216.

Video camera 214 is coupled to the wires at the distal end of video stylet 210. In many embodiments, a light source (not depicted for clarity) may be co-located with video camera 214 and coupled to the wires. In certain embodiments, light source control unit 218 is coupled to one or more of the wires to control the light source, such as, for example, one or more light-emitting diodes (LEDs), etc.

The cross section for flexible segment 210F depicts sheath 212, shield 211 and wires 232. Sheath 212 made be manufactured from solid polyvinyl chloride (PVC) to protect the cables from damage, such as, for example, fraying, etc. Shield 211 may include one or more layers of wire, aluminum foil and/or mylar. Wires 232 may be single or multiple strands of copper wire that are clad with high-resistance insulation material, such as, for example, a dielectric material, etc.; certain wires may be unclad. In many embodiments, the wires include a ground wire, a power wire, and two or more signal wires; the signal wires may be untwisted or twisted pairs.

The cross section for malleable segment 210*m* depicts sheath 213, malleable wire 230 and wires 232. Sheath 213 made be manufactured from polyolefin (e.g., heat shrink tubing) to protect the cables from damage, such as, for example, fraying, etc. Malleable wire 230 may be manufactured from a malleable metal, such as, for example, aluminum, etc.; in many embodiments, malleable wire 230 weighs about 16 to 18 grams. Wires 232 may be single or multiple strands of copper wire that are clad with high-resistance insulation material, such as, for example, a dielectric material, etc.; certain wires may be unclad. In many embodiments, the wires include a ground wire, a power wire, and two or more signal wires; the signal wires may be untwisted or twisted pairs.

Advantageously, the diameter of the malleable segment 210m is smaller than the diameter of the flexible segment 210E due, at least in part, to the absence of shield 211. In certain embodiments, all of the wires 232 may be twisted together to further reduce the diameter of the malleable segment 210m.

The view of the distal end is a view of the front end of video camera 214 including lens 217. In this embodiment, the light source includes multiple LEDs 219 surrounding lens 217.

Figure 6:
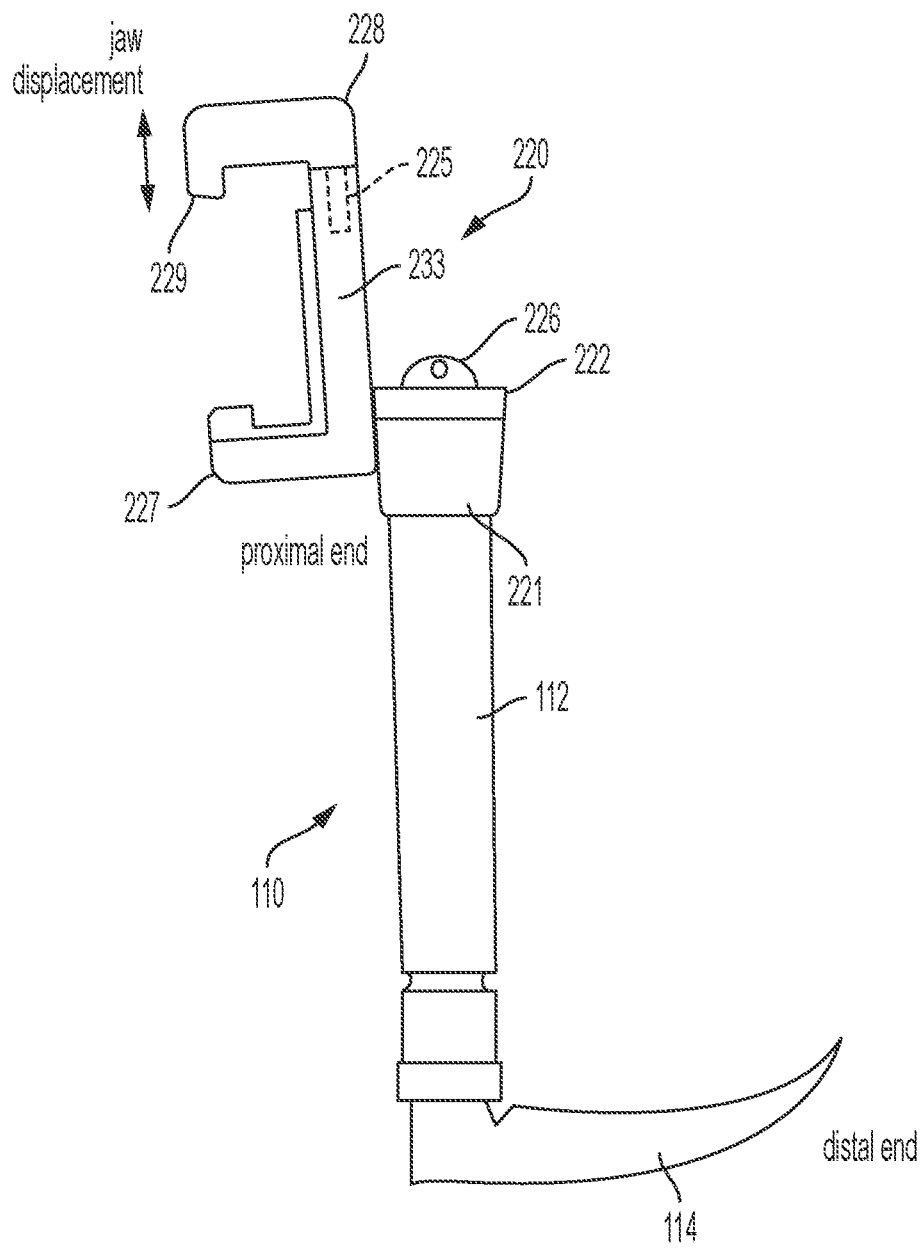
FIG. 6 depicts a laryngoscope and a holder of an LES, in accordance with an embodiment of the present disclosure.
Figure 7A:
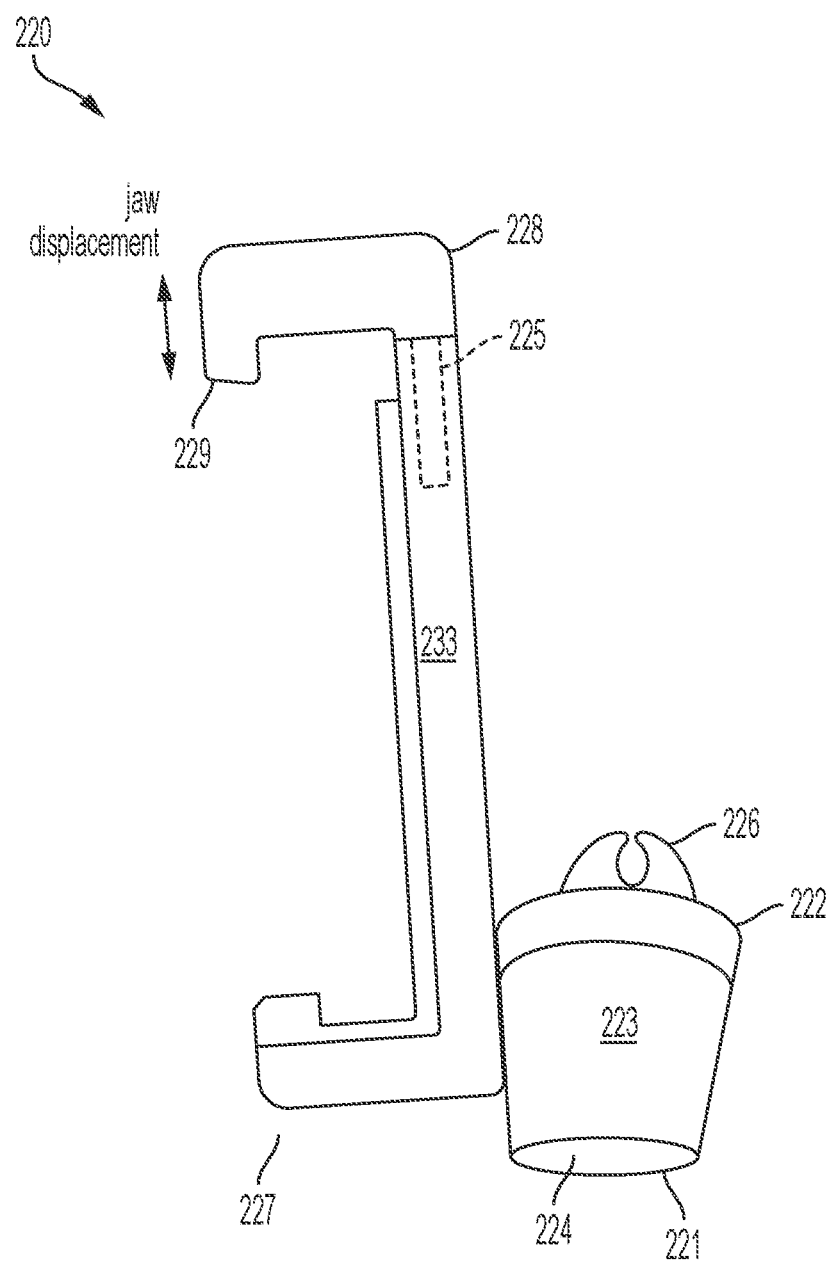
FIGS. 7A, 7B and 7C depict a holder of an LES, in accordance with embodiments of the present disclosure.
Figure 7B:
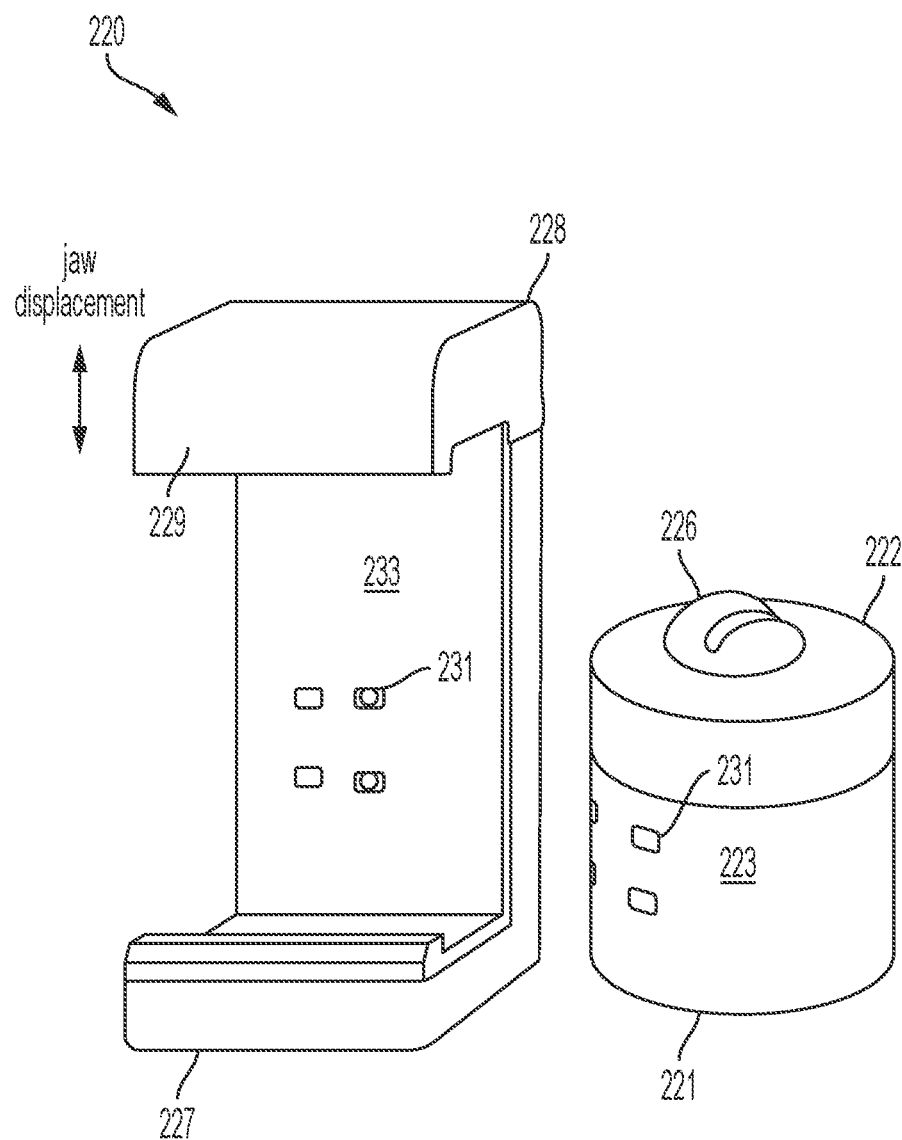
Figure 7C:
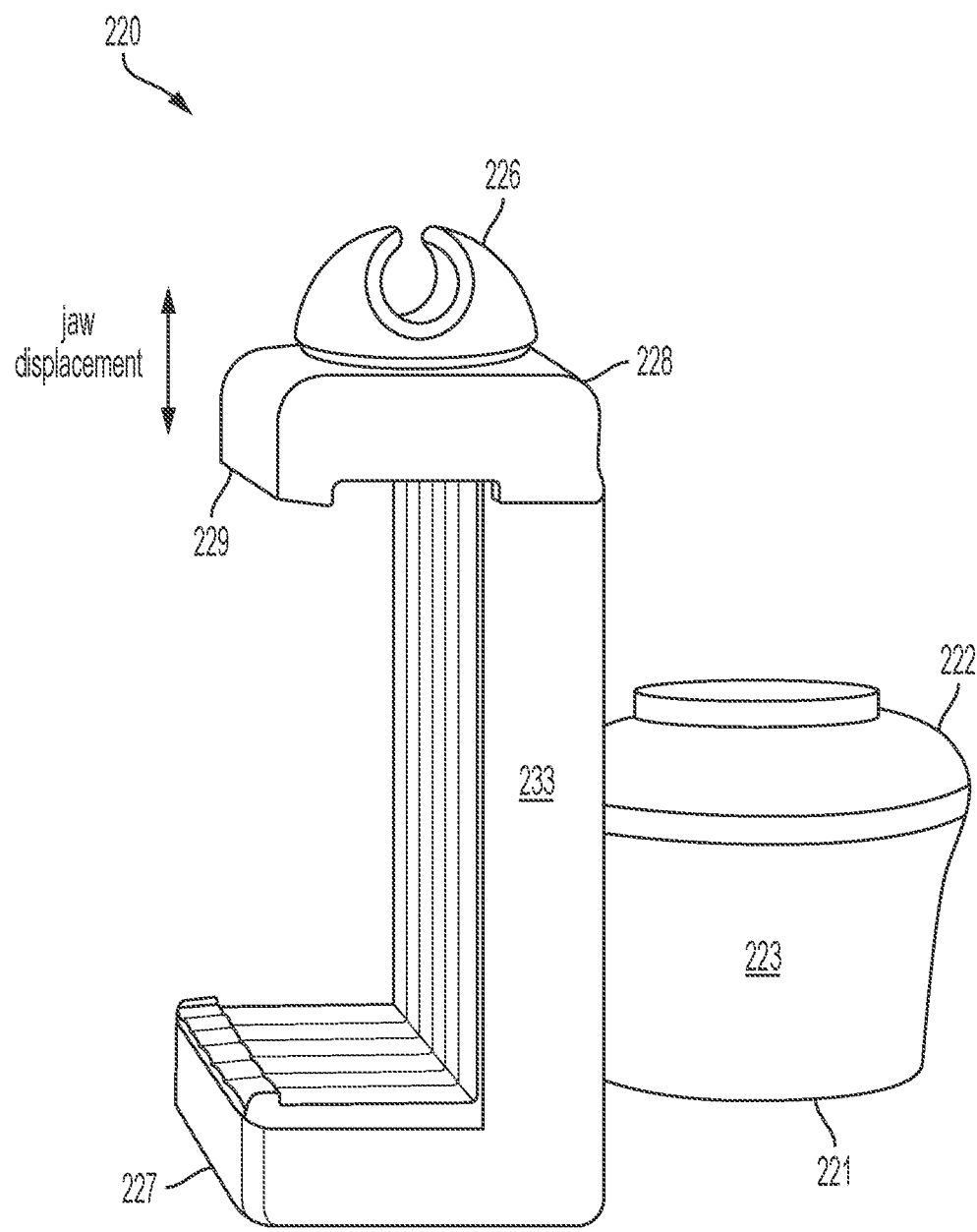

FIG. 6 depicts laryngoscope 110 and holder 220, in accordance with an embodiment of the present disclosure, while FIGS. 7A, 7B and 7C depict holder 220, in accordance with embodiments of the present disclosure.

As described above, laryngoscope 110 includes handle 112, blade 114 and connector 116 that attaches blade 114 to the lower end of handle 112, while holder 220 includes end cap 222 and adjustable mount 228.

End cap 222 is "fixedly" connected to adjustable mount 228. The connection may include glue, epoxy, cable ties, screws, bolts and nuts, rivets, straps, bands, a dovetail connection, etc. For example, cable ties may be used with co-operating holes 231 in end cap 222 and adjustable mount 228, as depicted in FIG. 7B. End cap 222 has a body 223 that defines a central cavity and lower edge 221 that defines lower opening 224 leading to the central cavity. End cap 222 removably attaches holder 220 to an upper end of handle 112 of laryngoscope 110. Lower opening 224 has a diameter that conforms to the diameter of the upper end of handle 112 of laryngoscope 110, which preferably fills the central cavity when end cap 222 is attached (e.g., 39 mm, etc.). End cap 222 may be manufactured from rubber, plastic, etc., in various central cavity sizes and lower opening diameters to accommodate different diameter laryngoscope handles.

Adjustable mount 228 releasably secures electronic device 120 to holder 220, and includes fixed jaw 227 and adjustable jaw 229. Positioning device 225, disposed within body 233 of adjustable mount 228, controls the displacement of adjustable jaw 229 along the longitudinal axis of adjustable mount 228. Positioning device 225 may include a spring-loaded ratcheting-type mechanism with a lock button or switch (not shown for clarity) that provides a number of predetermined locked positions or displacements for adjustable jaw 229. Other types of mechanisms are also supported. Adjustable mount 228 may be manufactured from plastic, aluminum, etc., and is sized appropriately to secure electronic device 120 (e.g., 6 inches×3 inches×0.5 inches). For example, the total displacement of adjustable jaw 229 along the longitudinal axis of adjustable mount 228 may be about 4 inches.

Holder 220 may include guide 226 to support a portion of video stylet 210. In the embodiment depicted in FIG. 6, guide 226 is disposed on an upper portion of end cap 222, while in the embodiment in FIG. 7C, guide 226 is disposed on an upper portion of adjustable mount 228.

The following embodiments are combinable.

In one embodiment, a laryngoscope enhancement system includes a holder and a video stylet. The holder includes an adjustable mount and an end cap. The adjustable mount is configured to releasably secure an electronic device with a display. The end cap is fixedly connected to the adjustable mount, and defines a central cavity with a lower opening. The end cap is configured to removably attach the holder to an upper end of a laryngoscope handle, and the lower opening has a diameter conforming to a diameter of the upper end of the laryngoscope handle. The video stylet includes a number of wires, a connecter coupled to the wires, a flexible segment, a malleable segment and a video camera coupled to one or more of the wires. The connector is removably attachable to an electronic device. The flexible segment includes a flexible sheath enclosing the wires. The malleable segment includes a malleable sheath enclosing a malleable wire and the wires. The malleable sheath has a smaller diameter than the flexible sheath.

In another embodiment of the laryngoscope enhancement system, the malleable wire extends along a length of the malleable segment.

In another embodiment of the laryngoscope enhancement system, the holder includes a guide configured to support the flexible segment of the video stylet.

In another embodiment of the laryngoscope enhancement system, the guide is disposed on an upper portion of the adjustable mount.

In another embodiment of the laryngoscope enhancement system, the guide is disposed on an upper portion of the end cap.

In another embodiment of the laryngoscope enhancement system, the video stylet further comprises an additional connector, coupled to the wires, having a different electrical interface than the connector.

In another embodiment of the laryngoscope enhancement system, the additional connector removably connectable to an additional electronic device.

In another embodiment of the laryngoscope enhancement system, the electronic device is a smart phone and the additional electronic device is a display.

In another embodiment of the laryngoscope enhancement system, the video stylet includes a light source coupled to at least one wire, and the flexible segment includes a light source control unit coupled to the least one wire.

In another embodiment of the laryngoscope enhancement system, the light source includes a plurality of light emitting diodes (LEDs) that surround a lens of the video camera.

In one embodiment, an intubation system includes an endotracheal tube (ETT), an electronic device with a display, and an enhanced laryngoscope. The ETT has an inner diameter. The enhanced laryngoscope includes a blade, a handle connected to the blade, a holder and a video stylet. The handle has an upper end and a diameter. The holder includes an adjustable mount and an end cap. The adjustable mount releasably secures the electronic device. The end cap defines a central cavity with a lower opening. The end cap is removably attached the upper end of the handle. The lower opening has a diameter conforming to the diameter of the handle. The video stylet includes a number of wires, a connecter coupled to the wires, a flexible segment, a malleable segment and a video camera coupled to one or more of the wires. The connector is removably attachable to the electronic device. The flexible segment includes a flexible sheath enclosing the wires. The malleable segment includes a malleable sheath enclosing a malleable wire and the wires. The malleable sheath has a smaller diameter than the flexible sheath.

In another embodiment of the intubation system, the malleable wire extends along a length of the malleable segment.

In another embodiment of the intubation system, the holder includes a guide configured to support the flexible segment of the video stylet.

In another embodiment of the intubation system, the guide is disposed on an upper portion of the adjustable mount.

In another embodiment of the intubation system, the guide is disposed on an upper portion of the end cap.

In another embodiment of the intubation system, the video stylet further comprises an additional connector, coupled to the wires, having a different electrical interface than the connector.

In another embodiment of the intubation system, the additional connector removably connectable to an additional electronic device.

In another embodiment of the intubation system, the electronic device is a smart phone and the additional electronic device is a display.

In another embodiment of the intubation system, the video stylet includes a light source coupled to at least one wire, and the flexible segment includes a light source control unit coupled to the least one wire.

In another embodiment of the intubation system, the light source includes a plurality of light emitting diodes (LEDs) that surround a lens of the video camera.

While implementations of the disclosure are susceptible to embodiment in many different forms, there is shown in the drawings and will herein be described in detail specific embodiments, with the understanding that the present disclosure is to be considered as an example of the principles of the disclosure and not intended to limit the disclosure to the specific embodiments shown and described. In the description above, like reference numerals may be used to describe the same, similar or corresponding parts in the several views of the drawings.

In this document, relational terms such as first and second, top and bottom, and the like may be used solely to distinguish one entity or action from another entity or action without necessarily requiring or implying any actual such relationship or order between such entities or actions. The terms "comprises," "comprising," "includes," "including," "has," "having," or any other variations thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises . . . a" does not, without more constraints, preclude the existence of additional identical elements in the process, method, article, or apparatus that comprises the element.

Reference throughout this document to "one embodiment," "certain embodiments," "an embodiment," "implementation(s)," "aspect(s)," or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C." An exception to this definition will occur only when a combination of elements, functions, steps or acts are in some way inherently mutually exclusive. Also, grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth. References to items in the singular should be understood to include items in the plural, and vice versa, unless explicitly stated otherwise or clear from the text.

Recitation of ranges of values herein are not intended to be limiting, referring instead individually to any and all values falling within the range, unless otherwise indicated, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," "for example," or the like) provided herein, is intended merely to better illuminate the embodiments and does not pose a limitation on the scope of the embodiments. No language in the specification should be construed as indicating any unclaimed element as essential to the practice of the embodiments.

For simplicity and clarity of illustration, reference numerals may be repeated among the figures to indicate corresponding or analogous elements. Numerous details are set forth to provide an understanding of the embodiments described herein. The embodiments may be practiced without these details. In other instances, well-known methods, procedures, and components have not been described in detail to avoid obscuring the embodiments described. The description is not to be considered as limited to the scope of the embodiments described herein.

In the following description, it is understood that terms such as "first," "second," "top," "bottom," "up," "down," "above," "below," and the like, are words of convenience and are not to be construed as limiting terms. Also, the terms apparatus, device, system, etc. may be used interchangeably in this text.

The many features and advantages of the disclosure are apparent from the detailed specification, and, thus, it is intended by the appended claims to cover all such features and advantages of the disclosure which fall within the scope of the disclosure. Further, since numerous modifications and variations will readily occur to those skilled in the art, it is not desired to limit the disclosure to the exact construction and operation illustrated and described, and, accordingly, all suitable modifications and equivalents may be resorted to that fall within the scope of the disclosure.

What is claimed is:

1. A laryngoscope enhancement system, comprising:
a holder, including:
an adjustable mount configured to releasably secure an electronic device with a display, and an end cap, fixedly connected to the adjustable mount, defining a central cavity having a lower opening, the end cap configured to removably attach the holder to an upper end of a laryngoscope handle, the lower opening having a diameter conforming to a diameter of the upper end of the laryngoscope handle; and a video stylet, including:

a plurality of wires, a connecter, coupled to the plurality of wires, removably attachable to an electronic device, a flexible segment including a flexible sheath enclosing the plurality of wires, a malleable segment including a malleable sheath enclosing a malleable wire and the plurality of wires, the malleable sheath having a smaller diameter than the flexible sheath, and a video camera coupled to one or more of the plurality of wires.

2. The system according to claim 1, where the malleable wire extends along a length of the malleable segment.

3. The system according to claim 2, where the holder further includes a guide configured to support the flexible segment of the video stylet.

4. The system according to claim 3, where the guide is disposed on an upper portion of the adjustable mount.

5. The system according to claim 3, where the guide is disposed on an upper portion of the end cap.

6. The system according to claim 2, where the video stylet further comprises an additional connector, coupled to the plurality of wires, having a different electrical interface than the connector.

7. The system according to claim 6, where the additional connector is removably connectable to an additional electronic device.

8. The system according to claim 7, where the electronic device is a smart phone and the additional electronic device is a display.

9. The system according to claim 2, where the video stylet includes a light source coupled to at least one of the plurality of wires, and the flexible segment includes a light source control unit coupled to the at least one of the plurality of wires.

10. The system according to claim 9, where the light source includes a plurality of light emitting diodes that surround a lens of the video camera.

11. An intubation system, comprising:

an endotracheal tube having an inner diameter;

an electronic device with a display; and a laryngoscope, including:

a blade, a handle, connected to the blade, having an upper end and a diameter, a holder, including:

an adjustable mount releasably securing the electronic device, and an end cap defining a central cavity having a lower opening, the end cap removably attached to the upper end of the handle, the lower opening having a diameter conforming to the diameter of the handle, and a video stylet, including:

a plurality of wires, a connecter, coupled to the plurality of wires, removably attachable to the electronic device, a flexible segment including a flexible sheath enclosing the plurality of wires, a malleable segment including a malleable sheath enclosing a malleable wire and the plurality of wires, the malleable sheath having a smaller diameter than the flexible sheath, and a video camera coupled to one or more of the plurality of wires.

12. The system according to claim 11, where the malleable wire extends along a length of the malleable segment.

13. The system according to claim 12, where the holder further includes a guide configured to support the flexible segment of the video stylet.

14. The system according to claim 13, where the guide is disposed on an upper portion of the adjustable mount.

15. The system according to claim 13, where the guide is disposed on an upper portion of the end cap.

16. The system according to claim 12, where the video stylet further comprises an additional connector, coupled to the plurality of wires, having a different electrical interface than the connector.

17. The system according to claim 16, where the additional connector is removably connectable to an additional electronic device.

18. The system according to claim 17, where the electronic device is a smart phone and the additional electronic device is a display.

19. The system according to claim 12, where the video stylet includes a light source coupled to at least one of the plurality of wires, and the flexible segment includes a light source control unit coupled to the at least one of the plurality of wires.

20. The system according to claim 19, where the light source includes a plurality of light emitting diodes that surround a lens of the video camera.

* * * * *